United States Patent
Qian et al.

(10) Patent No.: US 11,039,884 B2
(45) Date of Patent: Jun. 22, 2021

(54) MICROWAVE ABLATION DEVICE

(71) Applicants: The University of Sydney, New South Wales (AU); Western Sydney Local Health District, New South Wales (AU)

(72) Inventors: Pierre Qian, New South Wales (AU); Michael Anthony Barry, New South Wales (AU)

(73) Assignees: The University of Sydney, New South Wales (AU); Western Sydney Local Health District, New South Wales (AU)

( * ) Notice: Subject to any disclaimer, the term of this patent is extended or adjusted under 35 U.S.C. 154(b) by 648 days.

(21) Appl. No.: 15/580,615

(22) PCT Filed: Jun. 10, 2016

(86) PCT No.: PCT/AU2016/050480
§ 371 (c)(1),
(2) Date: Dec. 7, 2017

(87) PCT Pub. No.: WO2016/197206
PCT Pub. Date: Dec. 15, 2016

(65) Prior Publication Data
US 2018/0221089 A1  Aug. 9, 2018

(30) Foreign Application Priority Data
Jun. 12, 2015  (AU) ................................ 2015902225

(51) Int. Cl.
*A61B 18/18* (2006.01)
*A61B 18/00* (2006.01)

(52) U.S. Cl.
CPC ..... *A61B 18/1815* (2013.01); *A61B 2018/00029* (2013.01); *A61B 2018/00273* (2013.01);
(Continued)

(58) Field of Classification Search
CPC ............... A61B 18/18; A61B 18/1815; A61B 2018/1838; A61B 2018/1884; A61B 2018/1892
See application file for complete search history.

(56) References Cited

U.S. PATENT DOCUMENTS

| 6,210,367 B1 | 4/2001 | Carr |
| 7,566,341 B2 * | 7/2009 | Keller ........................ A61F 7/12 607/105 |

(Continued)

FOREIGN PATENT DOCUMENTS

| GB | 2503673 A | 1/2014 |
| JP | 08187297 | 7/1996 |

(Continued)

OTHER PUBLICATIONS

PCT/AU2016/050480, "International Search Report and Written Opinion", dated Aug. 5, 2016, 10 pages.

(Continued)

*Primary Examiner* — Ronald Hupczey, Jr.
(74) *Attorney, Agent, or Firm* — Kilpatrick Townsend & Stockton LLP

(57) ABSTRACT

A microwave ablation device (10) comprises a feed line (22), a microwave radiator and a device outer sheath (46) in which at least part of the feed line (22) is contained. The sheath (46) in use, allows an irrigation liquid to flow therethrough, wherein the feed line has a junction (38) with the radiator (22) has an outer conducting shield (28) terminating and insulated at the junction (38). The feed line (22) has a conductive core (32) that extends to the radiator (24). The conductive core forms a radiating element (34) electrically insulated from its surrounding environment. The radiator (24) is unbalanced.

15 Claims, 5 Drawing Sheets

(52) U.S. Cl.
CPC .............. *A61B 2018/00345* (2013.01); *A61B 2018/00511* (2013.01); *A61B 2018/00577* (2013.01); *A61B 2018/1861* (2013.01)

(56) References Cited

U.S. PATENT DOCUMENTS

| | | | |
|---|---|---|---|
| 8,382,750 B2 * | 2/2013 | Brannan | H04W 64/003 606/34 |
| 2012/0116486 A1 * | 5/2012 | Naga | A61B 18/1815 607/102 |
| 2012/0259326 A1 | 10/2012 | Brannan et al. | |
| 2015/0080875 A1 | 3/2015 | Kasprzyk et al. | |

FOREIGN PATENT DOCUMENTS

| | | | |
|---|---|---|---|
| JP | 2003514635 A | 4/2003 | |
| JP | 2009285463 A | 12/2009 | |
| JP | 2011511538 A | 4/2011 | |
| JP | 2012506300 A | 3/2012 | |
| JP | 2014514071 A | 6/2014 | |
| WO | 2011060200 A1 | 5/2011 | |

OTHER PUBLICATIONS 16806449.1, "Extended European Search Report", dated Jan. 23, 2019, 7 pages.

Japanese Application No. JP2018-516609, Office Action dated Aug. 25, 2020, 16 pages (10 pages of Original Document and 6 pages of English Translation).

\* cited by examiner

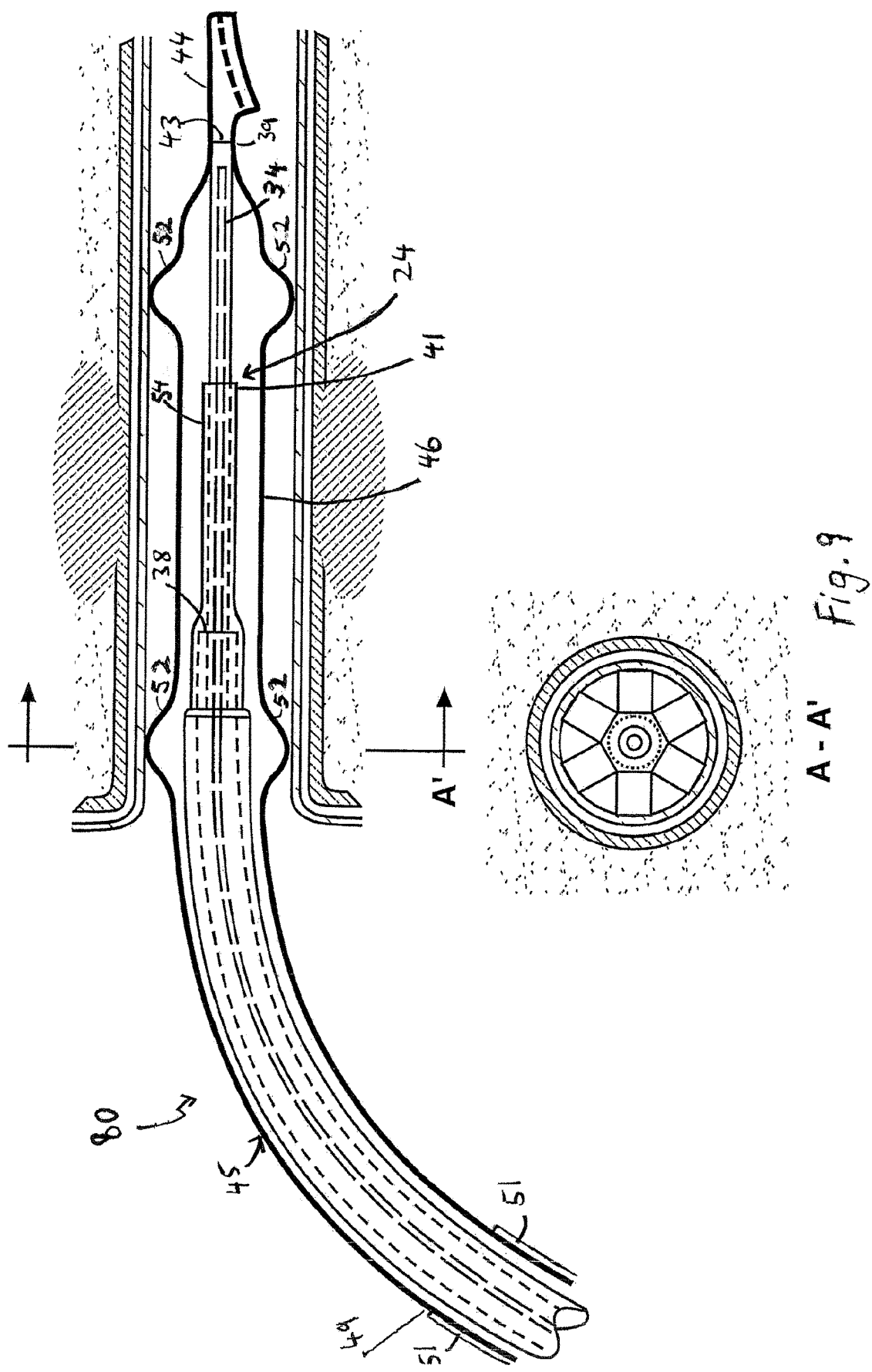

MICROWAVE ABLATION DEVICE

FIELD OF THE INVENTION

This invention relates to a microwave ablation device and a method of using such device. The invention may find application in the field of endovascular sympathectomy or denervation such as renal artery denervation. The invention may also find application in other fields of medical ablation including the treatment of atrial and ventricular arrhythmias.

BACKGROUND OF THE INVENTION

Hypertension is a significant medical condition that leads to morbidity and mortality from end organ injury, such as strokes, heart attack and kidney failure. Many patients require multiple medications for blood pressure control and for some patients, medications are poorly tolerated or ineffective altogether. Renal artery denervation has emerged as a possible treatment option to control hypertension in these patients who are refractory or intolerant of medical therapy. The procedure aims to eliminate the efferent and afferent nerves that relay neural messages between the kidneys and the central nervous system as these form essential components of neuro-hormonal reflexes that elevate blood pressure. The efferent and afferent nerves travel in the outer layer (i.e. adventitia) of the renal artery and the perinephric fat, mostly between 1 and 6 mm from the inner (i.e. luminal) surface of the renal arteries and can potentially be destroyed by endovascular catheter ablation.

Early clinical trials with radiofrequency catheter ablation for renal artery denervation showed promising results in blood pressure reduction. These results have fuelled interest and the development by various medical companies and research institutes of radiofrequency ablation catheters for this application.

More recently, a clinical trial of renal artery denervation compared a procedure performed by a renal denervation system developed by Medtronic with an operation sham control, and this failed to show significant benefit in blood pressure reduction. One hypothesis offered by experts in view of the disappointing results is that ineffective renal artery denervation occurred during this trial.

Prior art radiofrequency catheters used for renal artery denervation may have a disadvantage of injuring the full thickness of the renal artery before the renal nerves are affected. For this reason, conservative ablation of the artery is typically performed, thereby to avoid renal artery stenosis. This type of conservative ablation is however done at the cost of reducing the potential efficacy in denervating renal nerves with this energy source. For example, typically the catheters produce focal endovascular ablation lesions in a spiral configuration along a renal artery so as not to cause circumferential injury to the muscle layer, or media, of the artery, as this is what may lead to renal artery stenosis.

In light of the above, there is a need for an alternative type of ablation device.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In an embodiment of the invention there is provided an microwave ablation device comprising a feed line, a microwave radiator and a device outer sheath in which at least part of the feed line is contained, the sheath in use allowing an irrigation liquid to flow therethrough, wherein the feed line has a junction with the radiator and has an outer conducting shield terminating and insulated at the junction, the feed line having a conductive core that extends to the radiator, the conductive core forming a radiating element electrically insulated from its surrounding environment, wherein the radiator is unbalanced.

Preferably, the feedline is also unbalanced.

In a further embodiment, there provided a microwave ablation device comprising an electrically insulated feed line, a microwave radiator and a device outer sheath in which at least part of the feed line is contained, the sheath in use allowing an irrigation liquid to flow therethrough, wherein the outer conducting shield of the feed line terminates and is insulated from the conductive core and the surrounding environment, the feed line having a conductive core extending beyond the shield and becoming the radiator, the conductive core forming a radiating element electrically insulated from its surrounding environment, wherein the radiator is not matched to the impedance of the feed line and is unbalanced at the distal end.

According to another embodiment there is provided a microwave ablation device comprising a feed line, a microwave radiator, and an outer device sheath in which at least part of the feed line is contained, the sheath in use allowing an irrigation liquid to flow therethrough, wherein the feed line has an outer conducting shield terminating and insulated at its junction with the radiator, the feed line having a conductive core that extends without electro-magnetic interruption to the radiator, the conductive core forming a radiating element electrically insulated from its surrounding environment.

Each of the above embodiments may include the features of any one or both of the other embodiments.

For any of the above embodiments, the outer conducting shield may be electrically insulated at the junction by an insulating adhesive or sleeve that covers the distal end of the outer conducting shield. The outer conducting shield may also be insulated from an external surface of the device by the outer device sheath. Thus the outer conducting shield is insulated from to any adjacent conductive components, such as the radiator, the patient's blood pool and the outside environment.

Preferably, a distal end of the outer conducting shield is not connected to a choke.

The sheath may contain the microwave radiator and at least part of the feed line.

The sheath may further include one or more locating formations configured to centre and locate the device in use in a vessel.

The radiator may include an insulating layer extending over, or an insulating cover encasing, the radiating element.

The device may further be configured for the outer device sheath to be connected to the feed line and/or the insulated radiating element thereby to allow relative movement of the sheath to the feed line in use, wherein the one or more connecting formations comprise sections of slits in the sheath to form splines that deploy to form convex protrusions that interact with vessel walls.

Preferably the device has a distal end that includes an opening for the irrigation fluid to flow out of the device and over the radiator to cool the vessel. Preferably the opening is at a distal end of the feed line, so that the irrigation fluid can cool the feed line.

The microwave ablation device may be driven by a microwave energy source.

The microwave energy source may operate at 2.45 GHz, with a power output sufficient to produce circumferential thermal ablation of targeted neurological structures while enabling sparing of the tissue closer to the renal artery lumen, such as the renal artery wall, by cooling of said tissue closer to the renal artery by arterial blood flow and said irrigation fluid.

According to a further aspect there is provided a method of microwave ablation comprising:

introducing a distal end of a device, according to any embodiment defined above, into a human body;

locating the radiator of the device adjacent an area within the human body to be ablated; and transferring microwave energy to the radiator.

Preferably the microwave energy is transferred for a predetermined period of time. In one embodiment, the period of time is approximately or exactly 3 minutes. Preferably, the microwave energy is driven by a microwave energy source that operates at a said power output.

The area of the human body may be a renal artery.

The method may further comprise feeding the irrigation liquid to flow between the outer device sheath and the feed line, to cool the feed line while in use.

Preferably said irrigation liquid flows out of the distal end of the feedline to further cool said tissue closer to the renal artery lumen.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

Illustrative embodiments of the various aspects of the present invention will now be described by way of non-limiting example only, with reference to the accompanying drawings. In the drawings:

FIG. 9 shows a cross-sectional view of a microwave ablation device in accordance with a further example embodiment.

Where the Figures represent the same or similar features the same reference numerals will be used.

DETAILED DESCRIPTION OF THE EMBODIMENTS

Figure 1:
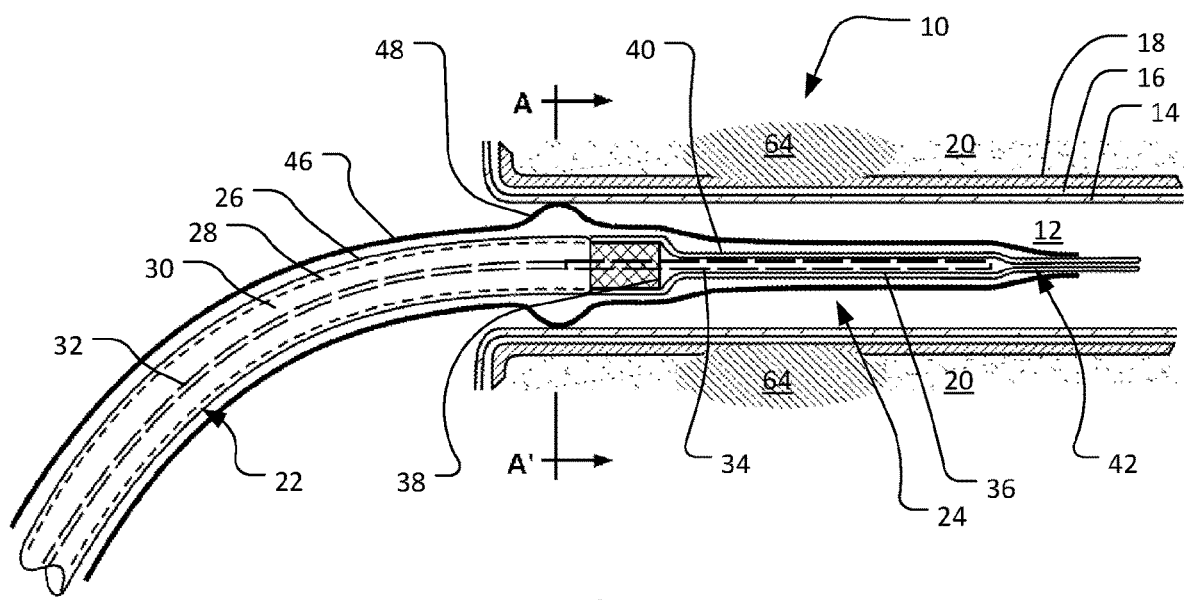
FIG. 1 shows a partial cross-sectional view of a microwave ablation device in accordance with an example embodiment.
Figure 3:
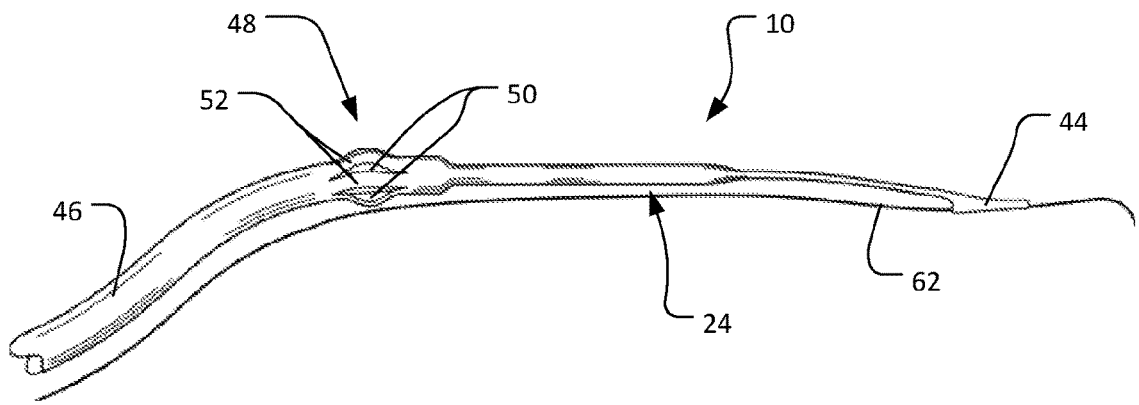
FIG. 3 shows a pictorial view of a microwave ablation device in accordance with an example embodiment and similar to that of FIG. 1 in a deployed state.
Figure 4:
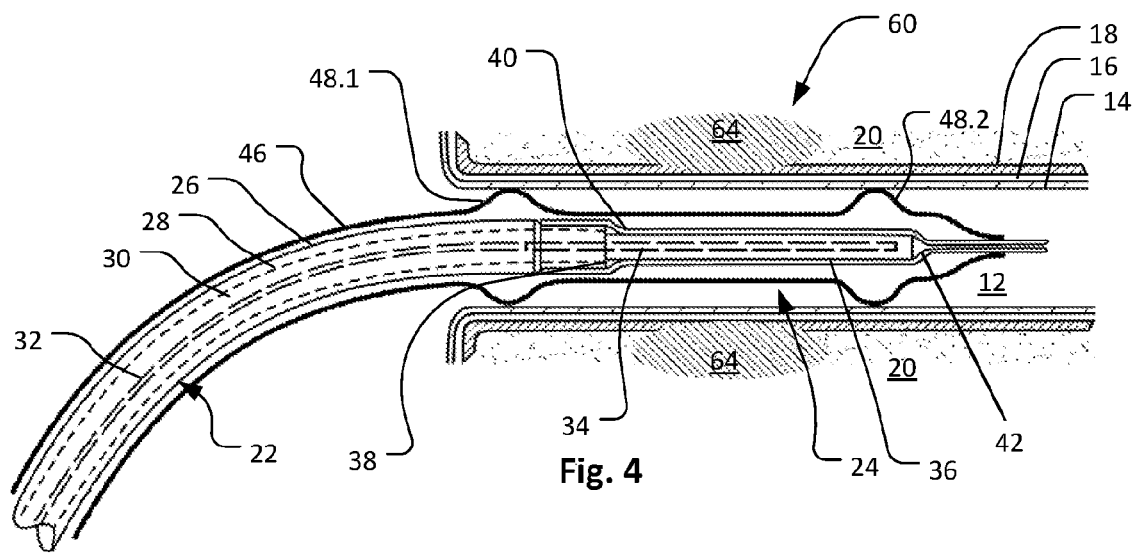
FIG. 4 shows a cross-sectional view of a microwave ablation device in accordance with another example embodiment.

Turning to FIGS. 1 and 3, a microwave ablation device 10 is shown. In this embodiment the ablation device 10 is a microwave emitting catheter used for microwave denervation of renal arteries. In FIG. 1, the microwave ablation device 10 is shown in a vessel, e.g., a renal artery 12, formed by various artery walls: the inner layer (or vessel intima) 14, the middle layer (or vessel media) 16 and the outer layer (or vessel adventitia) 18. Adjacent to the vessel adventitia 18 lies the renal nerves 20, which in this embodiment is to be ablated.

Although the device 10 is described with reference to denervation of renal arteries, a person skilled in the art will appreciate that the device may be used in other medical ablation applications.

The microwave ablation device 10 comprises a feed line 22 connected, in use, to an energy source (not shown), in particular a microwave energy source. The feed line 22 terminates in a radiator 24 (or antenna) having a single radiating element, which radiates microwave energy to the surrounding environment. As will become more apparent from the description below, the microwave energy is transmitted to the surrounding area and absorption produces heat. Blood flow dissipates this heat quickly, protecting the intima and media layers 14 and 16 of the artery walls, resulting in preferential heating of the renal artery adventitia layer 18 and deeper regions thereby to ablate the renal nerves 20 located in the deeper regions to the renal artery 12.

The feed line 22 may be a cable, for example, a co-axial cable which is well known to comprise, from the outer layers to the inner layers, an insulating outer sheath 26, an outer conducting shield 28, a tubular insulating layer 30 and a conductive core (also called an inner conductor) 32.

The radiator 24 has a radiating element 34 that has a diameter that is always less than the diameter of the feed line 22 and is concentric with the feed line 22. The radiating element is an extension of the conductive core 32 of the feed line 22, so has a constant diameter, being the same diameter as conductive core 32. The "junction" between the radiator 24 and feed line 22, indicated by reference numeral 38, is where the outer conducting shield 28 terminates. The radiating element 34 is electrically insulated from the surrounding environment. For example, the radiating element 34 may be encased in an insulating material shown in FIG. 1 by reference numeral 36. The radiating element 34 may alternatively be covered by or encased in a layer of insulating material. The insulating material may be PTFE (i.e. teflon), although any other suitable electrically insulating material which will tolerate the particular temperatures may be used e.g., FEP (fluorinated ethylene polymer).

At the junction 38 between the feed line 22 and the radiator 24, the outer conducting shield 28 is terminated and sealed by an insulative structural support component 40. As will be described in more detail below with reference to FIGS. 6A to 6C in which the structural support component 40 is best seen, this component 40 provides the device 10 at the junction with structural support and flexibility and acts as a cover of the radiator 24.

The device 10 does not have a choke attached to outer conducting shield at the distal end of the feed line 22. Thus, the conductive core extends without electro-magnetic interruption to the radiator. Further, there is no end-cap at the distal end of the radiating element 24, nor a ⅝ λ coil or any other structure for impedance matching attached to the radiator 24. As a result of not having a choke, the radiator radiates relatively more energy at the radial distance from the radiator at which denervation is to be performed. This is further aided by not having the end-cap or coil attached to the radiating element. By contrast the inclusion of such a choke would concentrate the radiation pattern closer to the radiating element, even the more so if an end cap or coil is attached to the radiating element. Such end-caps may take a variety of forms, but in effect add capacitance to the radiator element. For example, the end-cap may be electrically connected to the distal tip of the radiating element and from there feed proximally over some distal section of the radiating element, but radially insulated from the radiating element. Such coils, on the other hand typically are connected at one end to the outer conducting shield and at the other end to location along the length of the radiating element, eg about a ⅝ λ from the junction 38.

There is also no electrical shield (like a ground plane) or radials extending laterally from the outer conducting shield By omitting such shields and radials the maximum diameter of the device is kept to a minimum so as not to add unnecessary bulk or interfere with the vessel in which the ablation device is deployed.

Without a choke, coil, ground plane, radials, end cap or any other such structures, the device is significantly 'unbalanced' in that the load on the outer conducting shield 28 and the conductive core 32 (including the radiating element 34 portion of the conductive core 32) is not matched. This contrasts with conventional antenna design practice in which these structures are used to produce an antenna with minimal power loss and efficient transmission in the far field.

Also, with the radiating element 34 being insulated, energy cannot be dissipated through alternating current flow (ohmic heating) to the surrounding environment, i.e. blood flowing in the renal artery 12 or other irrigation fluid described later. The only energy dissipation from the radiating element 24 is accordingly by radiation. As will become apparent below, these factors result in a more favourable heating pattern across the area to be ablated and greater deployability, at the cost of comparatively higher loss of energy along the feed line 22 due to circulating currents (eddy currents) in the conducting shield 28, and consequent greater feed line 22 heating. Part of the favourability of the heating pattern is that it is generally spread, in the near field, across a greater length of the radiator, as opposed to being concentrated as a hot spot at one end of the radiator (as may be the case where a ground plane, choke, coil and/or end cap is employed). This results in providing a greater length over which perivascular nerves may be ablated. This may improve the durability of the denervation procedure by widening the gap that neuroregeneration would need to bridge to re-establish functional connections.

The cover 40 may carry a component 42 that may be an attachment or a continuation of the cover 40 or outer sheath 46. The component 42 carries a monorail segment 44 for tracking an angioplasty wire (e.g. a 0.014 inch angioplasty wire). The structural support cover may extend over the terminating end of the outer layers of the feed line 22 to the tip (and beyond) of the radiator 24. In one example embodiment the cover 40 is manufactured from a polyolefin material due to its features of being heat-shrinkable, thereby creating a tight fit. However, it will be appreciated that other suitable materials may be used such as PTFE (Teflon) or other high temperature plastics like FEP.

In the embodiment shown in FIG. 1, part of the device 10 is contained in an outer device sheath 46. The sheath 46 is typically manufactured from a suitable material that is soft and thin, e.g., a polymer such as polyolefin, which can generally be safely used in the human body.

The sheath 46, in this embodiment, comprises a locating formation 48 which acts as a centering mechanism and which is formed by linear slits 50 (best shown in FIGS. 2 and 3) along the length of the sheath 46 which form a section of splines 52 (see FIGS. 2 and 3) along part of the sheath 46. As the splines 52 are soft, when the feed line 22 is moved relative to the sheath 46, the splines 52 are deployed by expansion to form a convex protrusion against the inner walls 14 of the artery 12. The locating formation then secures and centrally locates the sheath 46, and with that, the radiator 24 and feed line 22 in place. Thus, the locating formation 48 adjusts to maintain contact pressure and concentricity with the local arterial wall 14. The collapsing of the mechanism is guaranteed by simply pulling the outer device sheath 46 back.

The outer device sheath 46 is sufficiently sized, i.e. it has a sufficient diameter, in comparison to the feed line 22, to allow for an irrigation or cooling liquid in use to pass between the insulating outer sheath 26 of the feed line 22 and the outer device sheath 46. Typically, a saline solution is pumped into and through the sheath 46, for it to exit into the artery 12 at the locating formation 48. As the saline solution flows along the length of the feed line 22, heat is removed from the device 10 to ensure that any clinically important temperature rises are addressed, and maintains the catheter lumens clear of blood to prevent thrombosis.

Figure 5A:
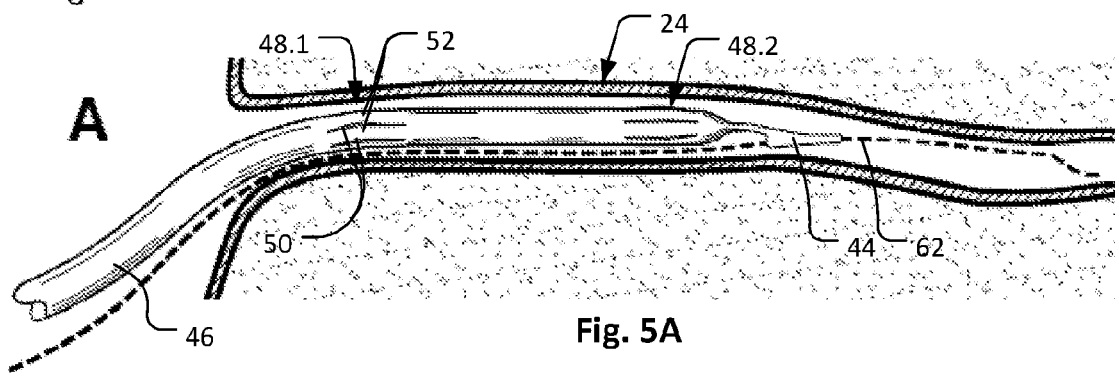
FIGS. 5A to 5C show pictorial views of a microwave ablation device in accordance with an example embodiment and similar to that of FIG. 3 with the outer device sheath in various states of deployment in an artery.
Figure 5B:
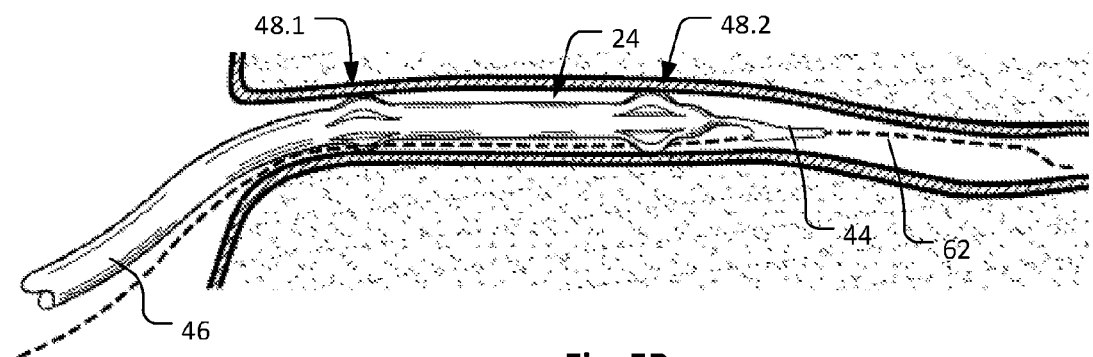
Figure 5C:
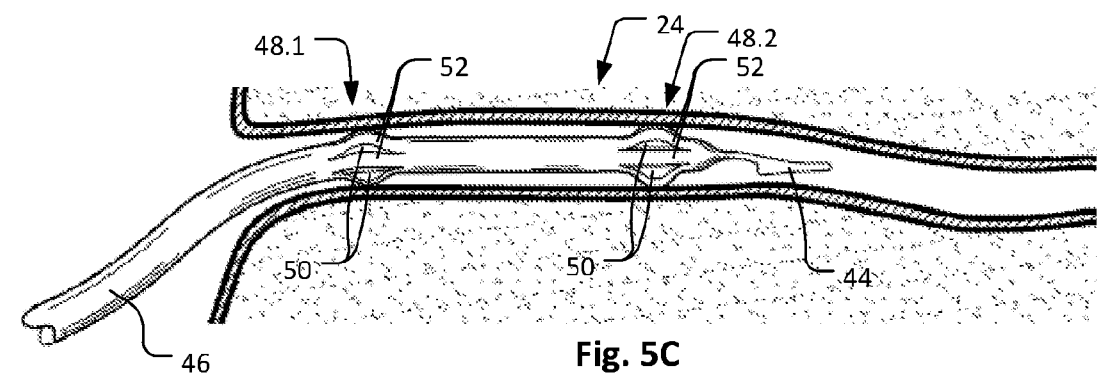

Turning to FIGS. 4 and 5A to 5C, another example embodiment of a microwave ablation device 60 is shown. The device 60 has the same or similar features as the device 10, and these features are accordingly indicated by the same reference numerals used in FIGS. 1 to 3. Also, like device 10, device 60 does not have a ground plane, choke, coil or end-cap. The outer device sheath 46 of the device 60 is however adapted to provide two locating formations 48.1 and 48.2, a distal locating formation 48.2 located towards the free tip (and connector) of the radiating element 24 and a proximal formation 48.1 closer to, or adjacent, a part of the feed line 22. Each of these locating formations 48.1 and 48.2 acts as part of a centering mechanism and is formed by linear slits 50 along the length of the outer device sheath 46 which form respective sections of splines 52 along parts of the sheath 46. Again, relative movement of the feed line 22 in a proximal direction with respect to the outer device sheath 46 (i.e. movement towards the aorta) is used to deploy these sections of splines into convex protrusions of the locating formations 48.1 and 48.2, allowing each to expand to the particular vessel (artery) size according to the amount that the outer device sheath 46 is moved relative to the feed line 22. As best shown in FIGS. 5A to 5C, the two locating formations 48.1 and 48.2 self-adjust to maintain equal contact pressure and concentricity with the local arterial wall by their design. During expansion, it is likely that one locating formation will expand first before the other. However, as soon as the first locating formation contacts the vessel wall, it is restrained by the wall and the other locating formation then expands till it too is providing the same pressure on the wall. This minimises the risk of trauma to the vessel at a place of natural or pathologic narrowing or dilatation.

Collapsing of the locating formations 48.1 and 48.2 are managed by simply moving the outer device sheath 46 relative to the feed line 22 in the proximal direction. This method of collapsing the formations 48.1 and 48.2 provides what is considered a safe way to reduce its diameter before removing the device 60.

Figure 2:
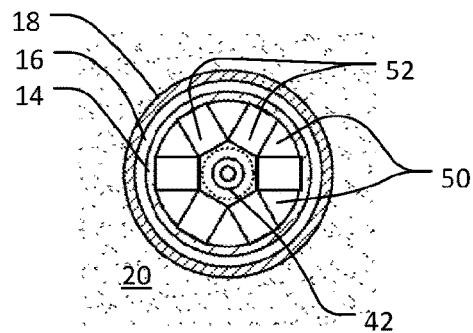
FIG. 2 shows a cross-sectional view along line A-A' of FIG. 1.

Similar to the description relevant to FIGS. 1 to 3, an irrigation liquid such as a saline solution is pumped into the sheath 46, with the saline solution in this embodiment passing, not only over the feed line 22, but also along most of the length of the radiating element 34 as contained by the insulating material 36. This assists with the removal of localised heat caused by radiation of the microwave energy, as well as the unbalanced nature of the device. It will further be appreciated that blood flow between the outer device sheath 46 and the inner walls 14 of the artery 12 (i.e. the luminal surface of the renal artery), which allow for further (and secondary) localised cooling during the ablation process. This flow of blood protects the intima and media (inner and middle) layers 16 and 18 of the artery 12 while deeper regions (e.g., including the outer or adventitia layer) containing the renal nerves are ablated.

The soft outer device sheath 46 is attached (secured) to the distal end of the feed line 22 or the distal end of the radiator 24. However the outer sheath 46 is otherwise free to move with respect to the feed line 22 in order to allow for the relative movement of the outer device sheath 46 in relation to at least the feed line 22, as well as to allow irrigation of the feed line 22 and the radiator 24 when the centering mechanism of the locating formation(s) is appropriately expanded. In the case of providing two formations 48.1 and 48.2 (e.g. FIG. 4, 5, 8, or 9) the soft outer sheath 46 is attached to the distal end of the radiator 24 rather than the feed line 22.

As mentioned above, the device may terminate in a monorail segment 44 which permits the delivery of the device over a conventional angioplasty wire 62. This angioplasty wire 62 is shown in FIGS. 3, 5A and 5B. Prior to deployment and ablation, the angioplasty wire is withdrawn so that it does not interfere with the microwave radiation.

Feed Line and Radiator Manufacturing

In one example embodiment, the feed line 22 of the device is formed from RG178 coaxial cable. As is well known, this consists of an outer FEP sheath of approximately 1.83 mm diameter+/−0.03 mm (i.e. the insulating outer sheath 26), a silver-plated copper braid (i.e. the outer conducting shield 28), a PTFE dielectric layer (i.e. the tubular insulating layer 30) of 0.86 mm outer diameter and a central core (the conductive core 32) of 0.3 mm diameter made of seven strands of silver-coated copper clad steel wire.

As mentioned, other materials may be used for the feed line 22, although it will be appreciated that they may have a larger diameter or smaller diameter. It is possible that smaller diameter feed lines, in particular where the diameter of the conductive core 32 (which also forms the radiating element 34 of the radiator 24) is too small, may not be able to deliver the required power output for denervation. In contrast, if the diameter is larger, the microwave ablation device may be less flexible and may occupy more space in the blood vessels which would result in more difficult usage and increased heat generation. It is expected that upscaling from a 1.8 mm cable to a 2.2 mm cable could reduce flexibility to a point where medical professionals such as cardiologist may opt not to use it. The type of conductive core has also been found to influence the ease of use of the device. For example, if a cable is used as the feed line 22 and the radiating element 34 with a single steel wire core rather than the seven strands of the RG178 cable, the relative stiffness of the microwave ablation device is increased to the point where it may be too difficult to conform the device to blood vessel changes.

In this example, the radiator 24 is formed by removing the FEP sheath (i.e. the insulating outer sheath 26), and the copper braid (i.e. the outer conducting shield 28), from the terminating end of the feed line 22 for a distance of about 23 mm. This exposes the PTFE dielectric (i.e. the tubular insulating layer 30), which, as mentioned, is about 0.86 mm in diameter. The PTFE dielectric is soft and flexible and forms the insulating layer 36 of the radiator. As the transition at this junction 38 from the full coaxial cable (feed line 22) to the PTFE dielectric is abrupt, this results in a potential structural weakness in the device that may cause difficulties with locating the device in an artery. For example, the abruptness may cause a potential bending point where the device 10, 60 will not follow the tip of the radiator 24 around corners, but instead will bend abruptly at that point and refuse to be advanced further into the site of interest.

The junction is strengthened by adding the structural support component 40 discussed above. For example, a small piece of tubing, which may be heat-shrinkable, is wrapped around a portion of the feed line 22. Typically, the FEP sheath (i.e. the insulating outer sheath 26) is removed for about 3 mm, exposing the copper braid (i.e. the outer conducting shield 28). The structural support component, in the form of a polyolefin (or other suitable material) tube is then placed over the exposed copper braid (i.e. the outer conducting shield 28) and overlaid on the PTFE dielectric (i.e. tubular insulating layer 30), and extends from the point of termination of the outer sheath 26 to at least beyond the junction. The tube may be an approximate length of 17 mm. The structural support component may provide a stepped and/or gradually tapering formation between the feed line 22 and its outer layer 26 and the insulated radiating element 34. The component provides the junction 38 with more support and makes the transition in stiffness more gradual to reduce the risks of kinking at this point during deployment into the renal artery.

Figure 6A:
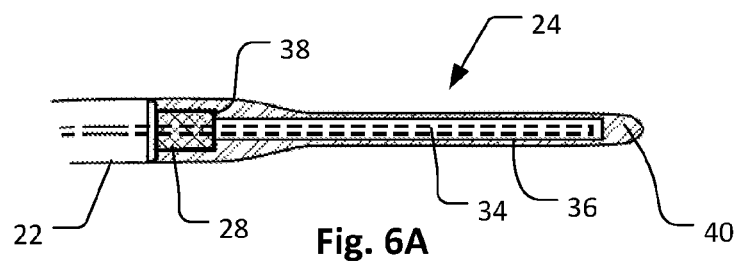
FIG. 6A shows a partial cross-sections of the distal end of a microwave ablation device, but not showing an outer sheath of the microwave ablation device, the figure illustrating a tapered structural support component in accordance with another embodiment, showing the device's radiator and its junction with the feed line, with the structural support component encasing the radiator.
Figure 6B:
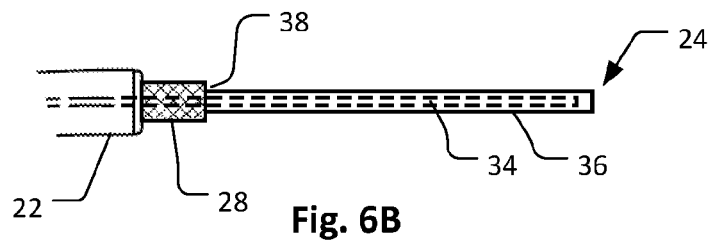
FIG. 6B shows a partial cross-section of only the device's radiator and its junction with the feed line of FIG. 6A, without the structural support component.
Figure 6C:
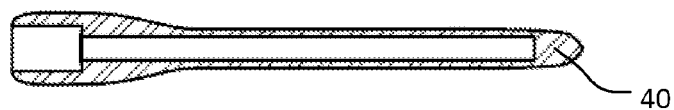
FIG. 6C shows a cross-section of only the structural support component which encases the radiator of FIG. 6B, thereby to form the end of the device as shown in FIG. 6A.
Figure 7:
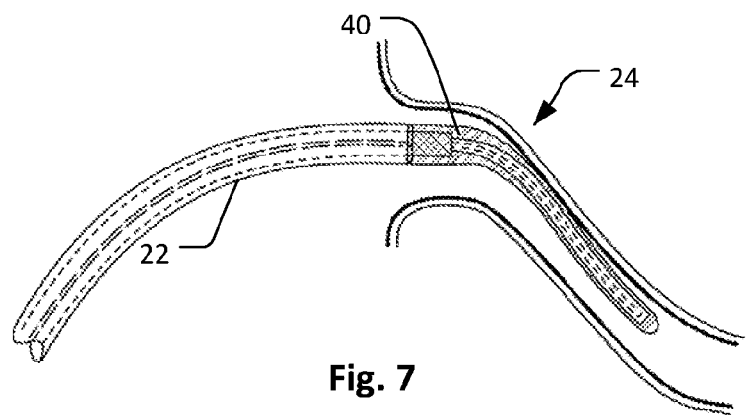
FIG. 7 shows the microwave ablation device of FIGS. 6A to 6C, without the outer sheath of the device so as to illustrate the effect of the support component when the device is being positioned in a renal artery prior to ablation.

In one example embodiment of the device, as shown in FIGS. 6A to 6C without the outer sheath 46, the structural support component 40 is manufactured as a cover that extends from the point of termination of the tubular insulating layer 30 at the distal end of the ablation device to the tip of the radiator 24. As is best shown in FIG. 6A, the component 40 extends over part of the outer conducting shield 28 and gradually tapers from its terminating end at the junction 38 to the radiator element 34 encased by the insulating layer 36. As mentioned, this component as a cover of the radiator 24 ensures that the junction does not hinder the process of locating the device in the renal artery, and ensures flexibility over the length of the device to reduce the risk of arterial and device damage. To assist in the understanding of the operation of component 40, the device of FIGS. 6A to 6C is illustrated in FIG. 7 without its outer sheath 46, as the device enters a renal artery. It should be borne in mind, however, that as the outer sheath 46 is omitted, FIG. 7 does not show the ideal disposition of the radiating element. Were the outer sheath included, the radiating element would be better centred in the artery due to the action of the splines 52 (as shown in FIGS. 5B and 5B), rather than being pressed against the arterial wall.

FIG. 9 shows a device 80 in accordance with a further embodiment of the invention. Device 80 is the same as device 60 of FIGS. 3 and 5A to 5C, except that device 80 also includes a support component 54. The support component 54 is the same as support component 40, except that rather than extending to the end of the radiator 24, the distal end 41 of the support component 54 ends about midway along the radiating element 34. This provides a stepped thickness along the length of the radiator 24 that results the radiator 24 being more flexible at its distal end than at the distal end 41 of the support component 54. In other embodiments, there may be multiple steps in thickness along the length of the radiator 24 and/or the cover 54 may have a tapering profile. The tapering of the support component 54 at the junction 38 and the stepped thickness along the radiator 24 each contribute to providing the radiator 24 with a greater flexibility at its distal end 41 than at its proximal end.

By having a more flexible distal end, the radiator 24 is better able to track the angioplasty wire and there may be improved centering of the radiating element 34. By comparison, a stiffer radiator may bias the radiating element 34 into one side of the vessel wall and overpower the soft centering splines 52.

FIG. 9 also illustrates further details in relation to the monorail segment 44. the monorail segment is in this embodiment attached to or is a continuation of the distal end 39 of the outer sheath 46, and is attached to the distal end 43 of the radiator 24. Having the radiator 24 stiffer towards its proximal end also provides the radiator 24 with enough structural integrity to push along the monorail without buckling.

In all embodiments described herein (but only illustrated in FIG. 9), the outer sheath 46 is more flexible towards the distal end 45 of the catheter 10, 60, 80 where it will sit inside the renal artery, than more proximally. This is because from a location 49 about 50-100 mm from the radiator 24, the outer sheath 46 is thicker. This increased thickness is achieved by having a second layer 51 or a transition or join to another material with stiffer properties which allow for greater transmission of push to advance the system over the monorail.

The thicker portion of outer sheath 46 extends back from the location 49 to fix to a haemostatic valve (not shown) at the proximal end (not shown) of catheter. Beyond the valve, the feed line 22 may be pulled with respect to the valve and outer sheath 46 to cause the splines 52 to protrude, or may be pushed to cause the splines 52 to retract. The valve includes an input which is used for introducing the saline solution to the catheter. The valve may include a Y connector, with one of the arms of the Y acting as the input. An example of such a part is part number 80303 manufactured by Qosina (Ronkonkoma, N.Y., USA).

The saline solution will flow from the input site, along the space between the coaxial cable (feed line 22) and the outer sheath 46 and emerge from the slits in the outer sheath in the formation that produces the splines 52. Irrigation of the catheter during ablation prevents excessive temperature rise in the catheter shaft and prevents ingress of blood and thrombosis in the catheter.

Having the catheter relatively more flexible towards its distal end (by having a relatively thinner outer sheath 46) enables the distal end 45 to follow the contour of the artery into which it is pushed, while the rest of the catheter is stiffer to enable the distal end 45 to be pushed into the artery.

The optimal length of the radiating element depends on the near field environment of the radiating element and the frequency of operation of the microwave generator. The structural support component may necessitate appreciable changes in the resonant length of the radiator 24 and the radiating element 34 at which maximal radiation occurs at the proposed operating frequency. This is due to the structural support component changing the nearby environment around the radiator to which the microwave field couples.

In this embodiment, the microwave ablation device 10, 60 and 80 is designed to work at a frequency of 2.45 GHz, and at this frequency, the length of a quarter wave radiating element would typically be about 4 mm. This is on the assumption that the radiator 24 is located in the blood pool. Because of the Teflon dielectric, which is on the radiating element to achieve electrical insulation, and because of the support component 54, the quarter wave length of the radiating element is increased to about 5 mm or more.

It will be appreciated that a half wave radiating element may also be selected, i.e. a length of about 11 mm, and that full wave radiating element may alternatively be selected, with a length of about 22 mm. However, radiating element lengths beyond a full wavelength may cause unwanted results such as bilobal radiation from the tip and root of the element.

A person skilled in the art will know that radiation patterns from a quarter wave, half wave or full wave radiator are not equal. Experiments by the present inventors have shown that a quarter wave radiating element radiates less energy into the near field than a half wave radiating element. In the case of half wave radiating element, approximately 11 mm in length, the energy is bunched in an approximately 5 mm zone, while the full wave radiating element radiates energy in a more spread pattern along the length of the radiating element. This pattern may have a length of about 15-19 mm for a full wave radiator measuring 22 mm in a matched environment, concentrated around the half-way point of the radiator.

Power Level

There is a large range in the power required to drive the catheter to perform optimal ablation, as the required power depends on the embodiment of this system. This is predominantly a result of feedline energy losses being dependent on the length of the feedline, and other factors. The proportion of the supplied power emitted by the radiator depends on the feedline energy losses. Therefore by keeping the catheter length to minimum, lower applied power is required. This may be as low 40-60 W for a short length (eg using an approximately 80 cm long catheter feedline) system and as high as 120-160 W for a longer system (eg using an approximately 140 cm long catheter feedline). The appropriate power required depends on the end radiator microwave output, the size of the renal artery, the rate of renal artery flow, and other patient factors. The power output is chosen to provide a high enough dose of microwave energy in order to ablate the perivascular tissues of the renal artery containing the renal nerves while being low enough to avoid injury to the arterial wall. Experimentally, a microwave energy dose delivery over about 3 minutes generally enables renal artery flow (along with saline irrigation) to keep the vessel luminal surface sufficiently cool to provide some sparing of injury to the renal artery wall under normal physiological conditions.

Irrigation

As mentioned, an irrigation liquid in the form of a saline irrigant/solution is used as a flow between the outer device sheath 46 and the feed line 22 and in some instances the insulated radiating element 24. The saline solution is fed, in one example, at a rate of about 20 mL/minute along part of the device inserted into the body. The aims of this feed are to prevent a clot forming in the device bore, and also to provide cooling for the feed line 22. In one embodiment, the power rating of the feed line 22 is 78 W continuous, in air. For such a feedline, the microwave ablation device 10, 60, 80 may be operated up to about 160 W if liquid saline cooling is used. This provides a sufficient level of cooling to permit the device to operate effectively without disturbance. Also, during operation of the device, the renal artery may benefit from the flow as it is flushed with the saline solution. Although the vessel (renal artery) may spasm during the procedure, the guaranteed flow caused by the saline solution through the device keeps the artery walls cooler than due to reliance on blood flow alone.

Use of the Microwave Ablation Device

In the example denervation use of the microwave ablation device 10, 60, 80 in a renal artery 12, the device is introduced via a peripheral artery, such as the femoral artery, within a guiding sheath used to engage the ostium of the renal artery. Following fluoroscopic confirmation of sheath engagement and definition of renal artery anatomy with radiopaque contrast injection, the device is introduced either directly or in an over the wire fashion into a segment of the renal artery. As mentioned above, the device may be delivered to the renal artery 12 through the use of a conventional angioplasty wire. Once in position, the locating formations 48.1 and 48.2 are deployed by moving the feed line relative to the outer device sheath until the locating formations 48.1 and 48.2 rest against the inner layers of the renal artery. The centering splines are capable of expanding to abut the walls of renal arteries of varying calibre, depending on how much relative movement occurs between the feed line and the outer device sheath. Angiographic estimation of renal artery calibre is made prior to spline deployment and graduated deployment of the splines is undertaken to centre device without causing arterial injury.

The microwave generator is then activated for a period of approximately 3 minutes during which microwaves radiate from the radiating element. Due to the radiating element being insulated, and as mentioned above, alternating current cannot flow from the element into the surrounding biological environment and ohmic energy losses through current flow are thereby curtailed. Due to the flow of the saline solution within the device, and the continued flow of blood in the artery, the area immediately adjacent the radiator, including the inner and middle layers of the renal artery is sufficiently cooled for ablation thereof not to occur. However, due to there being no cooling of the deeper regions, substantial heating will occur in these regions, resulting in ablation. For example, in both FIGS. 1 and 4, ablated areas are shown by reference numeral 64. In vitro testing of prototypes of the device on microwave phantom gel models of renal artery ablation, has shown to produce substantial heating with the potential to form lesions, while sparing the tissue adjacent to the renal artery lumen to a depth of about 1 mm depth. The depth of sparing is influenced by renal artery flow and other patient factors and is controllable by changing the dose and power of microwave energy delivery. Accordingly, this microwave ablation device, unlike radiofrequency energy probes/catheters, appears to be capable of denervating renal nerves without significant injury to the muscle layer and endothelial surface of the renal artery which are within approximately 0.5 mm deep from vessel lumen. Furthermore, because heating from microwave energy does not require catheter contact, it is possible to deliver a circumferential lesion to the outer layer 18 of the renal artery 12, and to deeper regions in the perinephric fat containing the renal nerves, with an appropriately centred microwave device of the invention, and to perform renal artery denervation with one energy application, potentially shortening and simplifying the procedure.

Prototype Example

Figure 8:
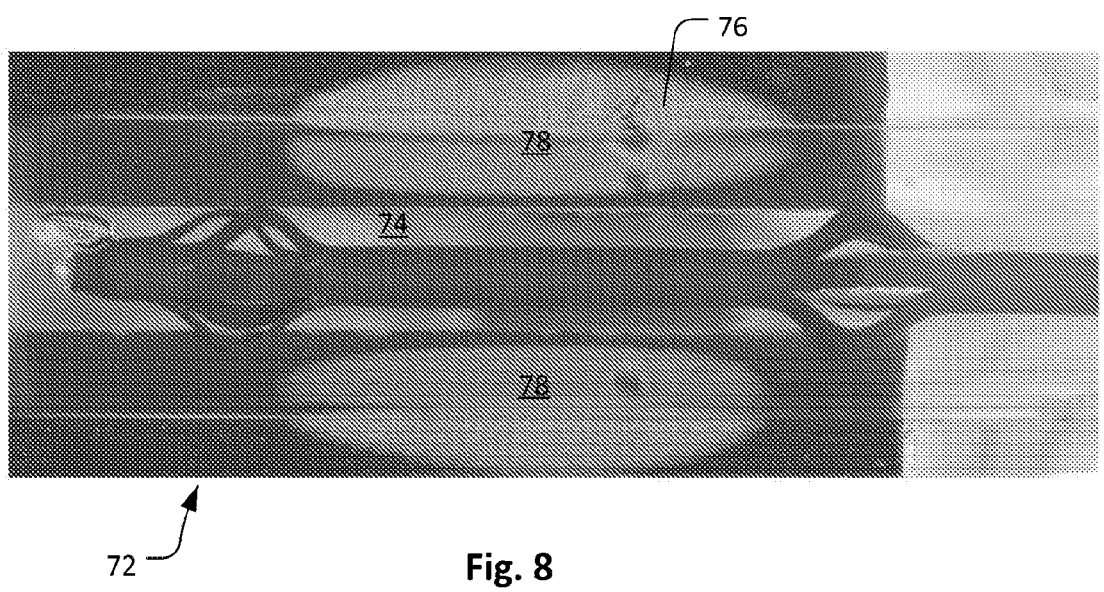
FIG. 8 shows an example prototype of a microwave ablation device in accordance with an example embodiment and in a model of a renal artery with heating patterns indicated.

A prototype of the microwave ablation device 70 is shown in FIG. 8 positioned in our longitudinal model 72 of a renal artery. This consisted of a tunnel (i.e. lumen) 74 in a microwave gel phantom material filled with 0.9% saline solution at 37° C. flowing at a rate of 0.5 L/min, which is the usual flow within the human renal artery. Within the phantom material is embedded a thermo-chromic liquid crystal sheet 76 which changes colour with temperatures between 50° C. and 78° C., permitting assessment of the thermal lesion by photography and in-house built software for colour-temperature conversion. The feedline consisted of a 137 cm long 50Ω coaxial cable. The microwave ablation device 70 was introduced into the lumen 74 of the model 72 of the renal artery and an ablation at 2.45 GHz, with 140 W power for 180 seconds was performed to yield the final lesion shown by reference numeral 78. As would be understood by a person skilled in the art, the elongate shape of the lesion, as shown in FIG. 8, is a visual indication of the elongate shape of the radiating pattern. 53° C. is the commonly accepted approximate temperature beyond which cell death occurs and the thermo-chromic liquid crystal sheet displays this temperature band as the transition between red and green colours. It can be observed that the microwave ablation spares the first 1-2 mm and extends to about 5-6 mm deep to the surface of the modelled renal artery lumen. This is sufficient to yield thermal injury to the majority of renal nerves, the bulk of which exist 1-6 mm from the vessel lumen while sparing the vessel intima and media which is within the first approximately 0.5 mm.

Method of Use In Vivo

An exemplary method by which the catheter 10, 60, 80 of the present invention may be used for renal artery denervation involves the following steps:

1. A vascular guide sheath (not shown) is inserted into a peripheral artery of a patient, usually the femoral artery. Any existing deflectable or non-deflectable guide sheath shaped to engage the renal artery may be used.

2. Systemic anticoagulation is administered to the patient to prevent intravascular thrombosis.

3. A 0.014" angioplasty wire is loaded onto the short monorail segment 44 of the catheter tip.

4. The catheter is flushed and de-aired under saline with irrigation at high flow (~60 mL/min) before introduction into the guide sheath. Irrigation at 30-60 mL/min is maintained after flushing.

5. The microwave ablation catheter is introduced via the vascular guide sheath after it is engaged in the renal artery such that its tip reaches the distal end of the vascular sheath.

6. The angioplasty wire is advanced down the renal artery or its branches and guided angiographically.

7. The ablation catheter is mono-railed over the angioplasty wire down to the site targeted for ablation.
8. The angioplasty wire is withdrawn.
9. The centering splines are deployed by pulling on the inner coaxial cable portion (feed line 22) of the catheter. The degree of displacement of the feed line 22 determines the extent to which the centering splines will protrude. This may be adapted to the size of the vessel as assessed with angiography.
10. Centering of the radiating element is checked in orthogonal fluoroscopic views.
11. Ablation is performed (eg 120-160 W for 3 min).
12. The splines are collapsed by pushing the feed line 22 relative to the sheath 46.
13. The catheter is withdrawn. If desired, further ablations more proximally in the renal artery can be performed by redeploying the splines when the catheter is at a more proximal location in the artery.

The microwave ablation device of the present invention is configured, in use, to allow for effective heating patterns that allow a single energy application, the heating pattern being spread across much of the length of the radiating element. Further, the heating pattern is more spread out (less circular/more elongate) than were the radiating element balanced and/or electromagnetically interrupted from the feedline by a choke and/or ground plane. The device is also configured to allow sufficient cooling of the feedline to enable high power to be used while renal artery flow and irrigant flow ensure protection of the inner layers of the artery from thermal injury, while denervation still occurs. By the use of soft splines as part of the locating formations, which can be deployed and collapsed manually, there is more control and graduation in the force exerted on the vessel wall in centering the catheter within the renal artery thus reducing the likelihood of vessel trauma.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A microwave ablation device comprising a feed line, a microwave radiator and a device outer sheath in which at least part of the feed line is contained, the device outer sheath in use allowing an irrigation liquid to flow therethrough, wherein the feed line has a junction with the microwave radiator and has an outer conducting shield terminating and insulated at the junction, the feed line having a conductive core that extends to the microwave radiator, a part of the conductive core forming the microwave radiator at a distal end thereof, electrically insulated from its surrounding environment, wherein the microwave radiator is not matched to the impedance of the feed line and is unbalanced at the distal end.

2. A microwave ablation device according to claim 1 wherein the device outer sheath contains the microwave radiator and at least part of the feed line.

3. A microwave ablation device according to claim 1 wherein the device outer sheath includes one or more locating formations configured to centre and locate the device in use in a vessel.

4. A microwave ablation device according to claim 1 including an insulating layer or an insulating cover extending over or encasing the microwave radiator.

5. A microwave ablation device according to claim 1 wherein the device is further configured for the device outer sheath to be connected to the feed line and/or the microwave radiator thereby to allow relative movement of the sheath to the feed line in use, wherein the device outer sheath includes one or more connecting formations comprising sections defined by slits in the device outer sheath, the sections configured to form splines that deploy to form convex protrusions that interact with vessel walls.

6. A microwave ablation device according to claim 1 wherein the microwave ablation device is arranged for connection to a microwave energy source.

7. A microwave ablation device according to claim 6 wherein the microwave energy source is operated at 2.45 GHz.

8. A microwave ablation device according to claim 1 wherein the outer conducting shield is not electromagnetically connected to a choke, ground plane, or radials.

9. A microwave ablation device according to claim 8 wherein a microwave energy source has a power output of between 40 W and 80 W for a feed line of approximately 80 cm and between 100 W and 160 W for a feed line length of approximately 140 cm.

10. A microwave ablation device according to claim 1 wherein the microwave radiator has a single radiating element.

11. A microwave ablation device according to claim 1 wherein the device is configured to be unbalanced in that different loads are on the outer conducting shield and conductive core, respectively.

12. A microwave ablation device according to claim 1 wherein the radiating element is not connected to an end-cap or a coil.

13. A method of microwave ablation comprising:
introducing a distal end of a device as claimed in claim 1 into a human body;
locating the microwave radiator of the device adjacent an area within the human body to be ablated; and
transferring microwave energy to the microwave radiator.

14. A method as claimed in claim 13 wherein the area of the human body is a renal artery.

15. A method as claimed in claim 13 further comprising feeding the irrigation liquid to flow between the device outer sheath and the feed line to cool the feed line while in use.

* * * * *